United States Patent [19]

Hauck et al.

[11] 4,053,596
[45] Oct. 11, 1977

[54] INDANPENTOL DERIVATIVES

[75] Inventors: Frederic Peter Hauck, Somerville; Joyce Reid, Highland Park; Venkatachala L. Narayanan, Hightstown; Christopher M. Cimarusti, Hamilton; Rudiger D. Haugwitz, Titusville, all of N.J.; Joseph E. Sundeen, Yardley, Pa.

[73] Assignee: E. R. Squibb & Sons, Inc., Princeton, N.J.

[21] Appl. No.: 649,116

[22] Filed: Jan. 14, 1976

[51] Int. Cl.$^2$ ............... C07D 211/14; A61K 31/445
[52] U.S. Cl. ............... 424/244; 260/293.56; 260/326.33; 260/326.5 R; 260/468 R; 260/468 H; 260/468 L; 260/476 C; 260/486 R; 260/487; 260/563; 260/570.8 R; 260/570.9; 260/571; 424/246; 424/248.55; 424/248.57; 424/250; 424/267; 424/274; 424/300; 424/308; 424/311; 424/313; 424/325; 424/330; 260/239 BC; 260/268 BC; 544/58; 544/59; 544/171; 544/173; 544/168
[58] Field of Search ............... 260/243 B, 247.7 A, 260/268 BC, 239 B, 293.56, 326.5 R, 573, 574, 584, 247.2 B, 326.33, 239 BC, 247.7 Z, 293.62; 424/246, 248.55, 248.57, 250, 267, 274, 244

[56] References Cited

U.S. PATENT DOCUMENTS

| 3,751,420 | 8/1973 | Hauck et al. .................. 260/293.56 |
| 3,894,031 | 7/1975 | Hauck et al. .................. 260/293.56 |
| 3,936,465 | 2/1976 | Hauck et al. .................. 260/293.65 |
| B 447,000 | 2/1976 | Hauck et al. .................. 260/293.56 |

Primary Examiner—Henry R. Jiles
Assistant Examiner—R. W. Ramsuer
Attorney, Agent, or Firm—Lawrence S. Levinson; Merle J. Smith; Burton Rodney

[57] ABSTRACT

Compounds are provided having the structure

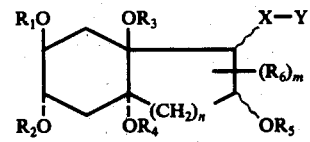

wherein $n$ is 1, 2 or 3, $m$ is 0, 1 or 2, $R_1$, $R_2$, $R_3$, $R_4$ and $R_5$ may be the same or different and can be hydrogen, lower alkyl, halo-lower alkyl, acyl, lower alkoxy-carbonyl

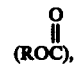

amido

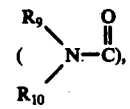

or lower alkoxyalkylene, X is a straight or branched bivalent aliphatic radical and Y is

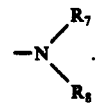

These compounds are useful in the treatment of hypertension.

18 Claims, No Drawings

INDANPENTOL DERIVATIVES

COMPOUNDS OF THE INVENTION

The present invention relates to indanyl, naphthyl and benzosuberanyl derivatives which have a lowering effect on blood pressure and are useful in the treatment of hypertension, in mammalian species, for example, rats and dogs. In addition, the compounds of the invention can be employed as antibiotics. A compound of formula I (below) as well as its physiologically acceptable acid salts may be compounded according to pharmaceutical practice in oral or parenteral dosage forms such as tablets, capsules, elixirs, injectables or powders for administration of about 100 mg. per day, preferably 125 mg. to 175 mg. per day, in 2 to 4 divided doses.

Furthermore, the compounds of this invention are useful as water softeners.

The compounds of the invention have the general formula:

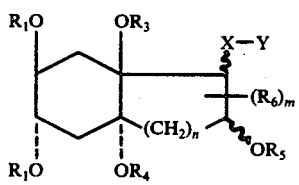

wherein $n$ is 1, 2 or 3, $m$ is 0, 1 or 2, $R_1$, $R_2$, $R_3$, $R_4$ and $R_5$ may be the same or different and represent hydrogen, acyl, lower alkyl, halo-lower alkyl, lower alkoxy-carbonyl

amido

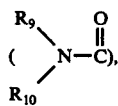

or lower alkoxyalkylene, $R_6$ is lower alkyl or monocyclic cycloalkyl, X is a single bond or a straight or branched chain bivalent aliphatic radical, and Y is

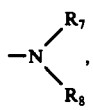

$R_7$ and $R_8$ may be the same or different, representing hydrogen, acyl, lower alkyl, halo-lower alkyl, monocyclic cycloalkyl, monocyclic cycloalkyl-lower, hydroxy-lower alkyl, monocyclic aryl, monocyclic aryl-lower alkyl, monocyclic heterocyclic.

The

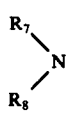

group may also form a heterocyclic radical.

X represents straight or branched chain bivalent aliphatic hydrocarbon groups having from zero to about ten carbon atoms, such as an alkylene group of the structure $(CH_2)_{n'}$ wherein $n'$ is zero to ten, such as methylene, ethylene, propylene, trimethylene, butylene, dimethylethylene, and the like. Furthermore, X can correspond to any of the lower alkyl groups exemplified hereinafter; $R_1$, $R_2$, $R_3$, $R_4$ and/or $R_5$ and $R_7$ and/or $R_8$ may be an acyl radical of a hydrocarbon carboxylic acid of less than twelve carbon atoms, which may be exemplified by the lower alkanoic acids (e.g, formic, acetic, propionic, butyric, valeric, trimethyl acetic and caproic acids), the lower alkenoic acids (e.g., acrylic, methacrylic, crotonic, 3-butenoic and senecioic acids), the monocyclic aryl-carboxylic acids (e.g., benzoic and toluic acids), the monocyclic aryl-lower alkanoic acids [e.g., phenacetic, β-phenylpropionic, α-phenylbutyric, and 5-(p-methylphenyl)pentanoic acids], the cycloalkyl carboxylic acids (e.g., cyclobutane carboxylic acid, cyclopentane carboxylic acid and cyclohexane carboxylic acid), the cycloalkenyl carboxylic acids (e.g., 2-cyclobutene carboxylic acid and 3-cyclopentene carboxylic acid), the cycloalkyl and cycloalkenyl-lower alkanoic acids [e.g., cyclohexaneacetic, α-cyclopentanebutyric, 2-cyclopenteneacetic and 3-(3-cyclohexane)pentenoic acid], and the like.

The alkanoic acids may include halogen substituents, for example, trifluoroacetic acid. In addition, other acyl groups which can be employed are angeloyl, veratroyl, vanilloyl, erythro-2-hydroxy-2-methyl-3-acetoxybutyryl, (1)-2-methylbutyryl; (d)-2-hydroxy-2-methylbutyryl; (d)-threo-2,3-dihydroxy-2-methylbutyryl and (1)-erythro-2,3-dihydroxy-2-methylbutyryl.

The term "lower alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Alkyl radicals substituted by F, Br, Cl or I are encompassed by the term halo-lower alkyl. Trifluoromethyl is a preferred halo-lower alkyl radical.

The term "monocyclic aryl" as employed herein contemplates monocyclic carbocyclic aryl radicals, for instance, phenyl and substituted phenyl radicals, such as lower alkyl phenyl (e.g., o-, m- or p-tolyl, ethylphenyl, butylphenyl, and the like), di(lower alkyl)phenyl (e.g., 2,4-dimethylphenyl, 3,5-diethylphenyl, and the like), halophenyl (e.g., chlorophenyl, bromophenyl, iodophenyl, fluorophenyl), o-, m- or p-nitrophenyl, dinitrophenyl, (e.g., 3,5-dinitrophenyl, 2,6-dinitrophenyl, and the like), trinitrophenyl (e.g., picryl).

The term "monocyclic aryoyl" includes any of the above aryl groups linked to a carbonyl group.

The term "monocyclic cycloalkyl" and "monocyclic cycloalkenyl" includes cyclic radicals containing from 3 to 6 ring members (e.g., cyclopropyl, cyclobutyl, cyclopentyl, cyclohexyl, cyclobutenyl and cyclohexenyl).

As indicated hereinbefore,

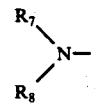

may form a heterocyclic radical. The symbols $R_7$ and $R_8$ may together represent the carbon (and hydrogen) and the oxygen, sulfur or nitrogen atoms which, with the nitrogen or carbon atoms in the above group, from a 5-, 6- or 7-membered nitrogen heterocyclic containing not more than one hetero atom in addition to the nitrogen already shown in the group and less than 21 atoms in the radical (excluding hydrogen). The heterocyclic radicals may include one to three substituents including lower alkoxy or lower alkyl as defined hereinafter; trihalomethoxy, such as trifluoromethoxy; trihalomethylmercapto, such as trifluoromethylmercapto; N,N-dialkylsulfamoyl groups, such as N,N-dimethylsulfamoyl; lower alkanoyl groups as defined hereinafter such as acetyl, propionyl, and the like; hydroxy; hydroxy-lower alkyl, such as hydroxymethyl, 2-hydroxyethyl, or the like; hydroxy-lower alkoxy-lower alkyl, such as 2-(2-hydroxyethoxy)ethyl, or the like; alkanoyloxy containing an alkanoyl as defined herein; alkanoyloxy-lower alkyl (up to about 14 carbons in the alkanoyl group), such as 2-heptanoyloxyethyl; carbo-lower alkoxy, such as carbomethoxy, carboethoxy, carbopropoxy, or the like; or 2-(alkanoyloxy-lower alkoxy) lower alkyl (with up to about 14 carbons in the alkanoyl group), such as 2-(decanoyloxyethoxy)-ethyl, or the like.

Illustrative of the heterocyclic radicals represented by $R_7$, $R_8$ or

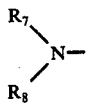

are the following: piperidino; (lower alkyl)piperidino [e.g., 2-, 3-, or 4-(lower alkyl)-piperidino or 4-(N-lower alkyl)piperidino such as 2-(ethyl)-piperidino or 4-(N-isopropyl)-piperidino]; di(lower alkyl)-piperidino [e.g., 2,4-, 2,5- or 3,5-di(lower alkyl)piperidino such as 2,4-dimethylpiperidino or 2,5-di-t-butyl piperidino]; (lower alkoxy)piperidino [e.g., 2-methoxypiperdino or 3-methoxypiperidino]; hydroxypiperidino [e.g., 3-hydroxy- or 4-hydroxypiperidino]; aminomethylpiperidino [e.g., 4-aminomethylpiperidino]; pyrrolidino; (lower alkyl)pyrrolidino [e.g., 3-methylpyrrolidino]; di(lower alkyl)pyrrolidino [e.g., 3,4-dimethylpyrrolidino]; (lower alkoxy)pyrrolidino [e.g., 2-methoxypyrrolidino]; morpholino; (lower alkyl)-morpholino [e.g., 3-methylmorpholino]; di(lower alkyl)morpholino [e.g., 3,5- dimethylmorpholino]; (lower alkoxy)morpholino [e.g., 2-methoxymorpholino]; thiamorpholino; (lower alkyl)-thiamorpholino [e.g., 3-methylthiamorpholino]; di(lower alkyl)-thiamorpholino [e.g., 3,5-dimethylthiamorpholino; (lower alkoxy)thiamorpholino [e.g., 3-methoxythiamorpholino]; piperazino; (lower alkyl)piperazino [e.g., $N^4$-methylpiperazino]; di(lower alkyl)piperazino [e.g., 2,5-dimethylpiperzino or 2,6-dimethylpiperazino]; (lower alkoxy)piperazino [e.g., 2-methoxypiperazino]; (hydroxy-lower alkyl)-piperazino [e.g., $N^4$-(2-hydroxyethyl)piperazino]; (alkanoyloxy-lower alkyl)piperazino wherein the alkanoyloxy group has up to 14 carbons [e.g., $N^4$-(2-heptanoyloxyethyl)piperazino or $N^4$-(2-dodecanoyloxyethyl)piperazino]; (hydroxy-lower alkoxy-lower alkyl)-piperazino [e.g., (hydroxy-methoxy-methyl)-piperazino]; (carbo-lower alkoxy)piperazino [e.g., $N^4$-(carbomethoxy-, carboethoxy-, or carbopropoxy)-piperazino]; homopiperazino; or $N^4$-(hydroxy-lower alkyl)homopiperazino [e.g., $N^4$-(2-hydroxyethyl)-homopiperazino]; piperidyl; (lower alkyl)piperidyl [e.g., 1-, 2-, 3- or 4-(lower alkyl)piperidyl, such as 1-N-methylpiperidyl or 3-ethylpiperidyl]; di(lower alkyl)-piperidyl [e.g., 2,4-, 2,5-, or 3,5-di(lower alkyl)piperidyl wherein lower alkyl is methyl, ethyl, n-propyl, isopropyl, etc.]; lower alkoxy piperidyl [e.g., 3-methoxypiperidyl or 2-ethoxypiperidyl]; hydroxy piperidyl [e.g., 3-hydroxy- or 4-hydroxypiperidyl]; aminomethylpiperidyl [e.g., 4-aminoethylpiperidyl]; pyrrolidyl; lower alkyl pyrrolidyl [e.g., 1-N- methylpyrrolidyl]; di(lower alkyl)pyrrolidyl [e.g., 2,3-dimethylpyrrolidyl]; lower alkoxy pyrrolidyl [e.g., 4-N-methoxypyrrolidyl]; morpholinyl; (lower alkyl)morpholinyl [e.g., 3-methylmorpholinyl]; di(lower alkyl)morpholinyl [e.g., 3-methyl-4-N-ethylmorpholinyl]; (lower alkoxy)morpholinyl [e.g., 2-ethoxymorpholinyl]; thiamorpholinyl; (lower alkyl)thiamorpholinyl [e.g., 3-ethylthiamorpholinyl]; di(lower alkyl)thiamorpholinyl [e.g., 3-methyl-4-N-ethylthiamorpholinyl]; lower alkoxy thiamorpholino [e.g., 3-methoxythiamorpholinyl]; piperazinyl; alkyl, dialkyl, alkoxy or hydroxy-lower alkyl substituted piperazinyl.

The N-oxides of the compounds of formula I wherein Y represents a nitrogen containing heterocyclic radical can be formed by reacting such formula I compounds with a peracid such as m-chloroperoxy benzoic acid, perbenzoic acid or monoperphthalic acid in a suitable solvent such as chloroform.

The compounds of formula I form acid addition salts by reaction with various inorganic and organic acids. These salts frequently provide convenient means for separating the product from the reaction mixture in which it is produced or from the solvent in which it is extracted in view of their insolubility in various media. Thus the product may be precipitated in the form of an insoluble salt and converted, by conventional techniques, to the free base or to another soluble or insoluble salt as desired.

Illustrative salts include the hydrohalides, such as hydrochloride, hydrobromide and hydroiodide, especially the first two, other mineral acid salts such as phosphate, sulfate, nitrate, etc., organic acid salts such as oxalate, tartrate, malate, maleate, citrate, pamoate, fumarate, camphorsulfonate, methanesulfonate, benzenesulfonate, toluenesulfonate, salicylate, benzoate, ascorbate, mandelate, or the like.

The compounds of formula I also form quaternary ammonium salts with lower alkyl halides, for example, methyl bromide, ethyl bromide and propyl iodide; benzyl halides, such as benzyl chloride; and dilower alkyl sulfates, such as dimethyl sulfate. To form the quaternary ammonium salts, the free base initially formed is intereacted with at least one equivalent of the desired alkylating agent.

Preferred are those compounds wherein n is 1 or 2, X is $(CH_2)_2$ or $(CH_2)_3$, Y is an amino group of a piperidino group with or without substituents, $R_1$, $R_2$, $R_3$, $R_4$ and $R_5$ are hydrogen or acyl and m is 0. Most preferred are those compounds wherein n is 1, X is $(CH_2)_2$ or $(CH_2)_3$, Y is dimethylamino or

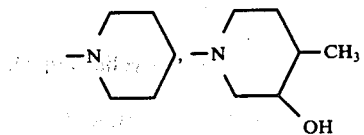

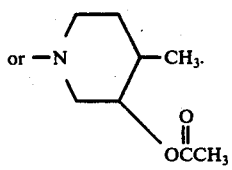

In all of the compounds of the invention, the $OR_1$, $OR_2$, $OR_3$ and $OR_4$ groups are axial and $OR_1$ and $OR_2$ are in trans configuration and $OR_3$ and $OR_4$ are in trans configuration.

The compounds of formula I includes all stereoisomers and mixtures thereof. Thus, in X-Y can be cis or trans to $OR_3$ and in $OR_5$ can be cis or trans to X-Y.

The compounds of Formula I of the invention may be prepared by a process which comprises forming a diene of the structure II.

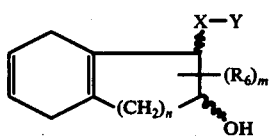

and converting the diene to the pentol or pentol derivatives of Formula I.

The pentol wherein $R_1$, $R_2$, $R_3$, and $R_4$ are hydrogen, can be formed by hydroxylating the diene to the corresponding pentol, for example, by reacting the diene with formic acid and aqueous hydrogen peroxide, at temperatures ranging from about 20° to 40° C to form a mixture of esters, and then subjecting the mixture of esters to basic hydrolysis by dissolving the mixture of esters in a solvent boiling below about 100° C, such as a monohydric alcohol containing up to four carbon atoms (e.g., methyl alcohol, ethyl alcohol, propyl alcohol, isopropyl alcohol or butyl alcohol), and then treating the solution with a base, such as an alkali metal of alkaline earth metal hydroxide or alkoxide (e.g., sodium hydroxide, potassium hydroxide, barium hydroxide, calcium hydroxide, sodium methoxide or calcium diethoxide) and heating the mixture to temperatures ranging from about 40° to about 80° C, to form the pentol of the structure:

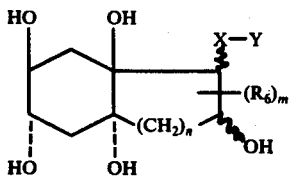

In the above reaction the hydrogen peroxide is employed in a molar ratio to the diene of within the range of from about 2.2:1 to about 15:1 and preferably from about 2.2:1 to about 5:1. The base is employed in a molar ratio to the mixture of esters of within the range of from about 2.2:1 to about 10:1 and preferably from about 2.2:1 to about 5:1.

The pentol of Formula III can be converted to the corresponding penta ester, i.e., where $R_1$, $R_2$, $R_3$, $R_4$ and $R_5$ are acyl as defined hereinbefore, by reacting the pentol with an acylating agent, such as a hydrocarbon carboxylic acid containing less than twelve carbon atoms as discussed hereinbefore, the acid anhydride thereof, or corresponding acyl halide, and an acid catalyst, such as perchloric acid, at a temperature within the range of from about −20° to about 0° C. The acid, acid anhydride or acyl halide is employed in a molar ratio to the pentol of within the range of from about 5:1 to about 20:1 and preferably from about 5:1 to about 10:1 and the acid catalyst is employed in a molar ratio to the pentol of within the range of from about 1.1:1 to about 2:1 and preferably about 1.1:1 to about 1.5:1.

In an alternative procedure, the diene of formula II can be converted to the corresponding pentol by dissolving the diene II in an organic carboxylic acid having up to about eight carbon atoms, such as acetic acid, treating the mixture with a silver salt corresponding to the acid, such as silver acetate (in a molar ratio of diene to silver salt of within the range of from about 1:2 to about 1:4 and preferably about 1:2) and iodine (in a molar ratio of diene to iodine of 1:1), heating the reaction mixture at a temperature of within the range of from about 60° to about 110° and preferably from about 80° to about 100°, to form a compound (depending on which acid and silver salt are employed) of the structure:

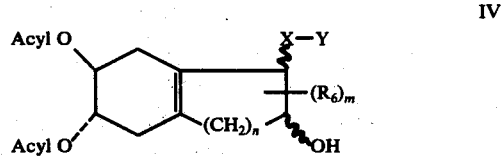

The above diester of the structure IV can be converted to the corresponding pentol by dissolving the diester in a suitable protonic solvent, such as ethyl alcohol, treating the solution with an excess of an aqueous base, such as aqueous sodium hydroxide or potassium hydroxide, to effect hydrolysis to the corresponding triol of the structure:

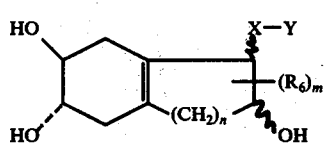

The above triol can be converted to the pentol by reacting with formic acid and hydrogen peroxide (as described hereinbefore), at temperatures ranging from about 20° to about 40° C, preferably about 35°, and then treating the mixture (free of solvent) with an alcohol and a base (as described hereinbefore) to form the pentol wherein OR's (1 to 4) are axial and each pair of OR's (1 and 2, and 3 and 4) are trans.

The pentols or derivatives thereof can also be prepared by reacting the diene II with formic acid and one equivalent of an oxidizing agent, such as aqueous hydrogen peroxide, and after removal of solvent, dissolving the residue in an alcohol-base as described hereinbefore to effect hydrolysis and form a triol olefin of the structure:

VI

-continued

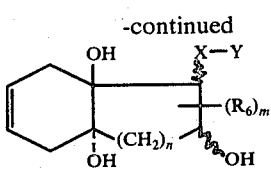

The above triol olefin can then be converted to the pentol as described hereinbefore with respect to the conversion of the triol olefin V.

Where Y is

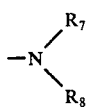

and at least one of $R_7$ and $R_8$ is or includes an aromatic ring, the pentols of the invention can be prepared by reducing a hydroxyalkyl compound of the structure:

VII

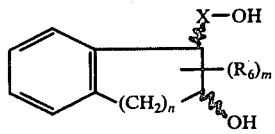

wherein X is lower alkylene as defined hereinbefore with respect to the corresponding diene, by reacting VII with a reducing metal, such as lithium or sodium in liquid ammonia in the presence of a proton source such as a lower alcohol, to form the corresponding hydroxyalkyl diene of the structure:

VIII

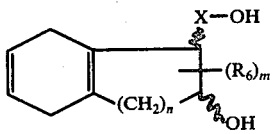

dissolving the hydroxyalkyl diene in a basic organic solvent, such as pyridine, cooling the solution to below 0°, treating the solution with a solution of p-toluene sulfonyl chloride in pyridine, in a molar ratio of diene to p-toluene sulfonyl chloride of within the range of from about 1:1 to about 1:1.5, and cooling to form the corresponding diene tosylate of the structure

IX

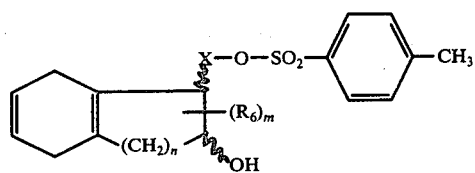

reacting the diene tosylate with an arylamine or substituted arylamine, aryl lower alkylamine or substituted aryl lower alkylamine or an amine of the structure

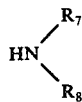

(in a molar ratio of tosylate to amine of within the range of from about 1:2 to about 1:5) in an aromatic solvent boiling below about 120° C, such as toluene or benzene to form an aminoalkyldiene of the structure:

X

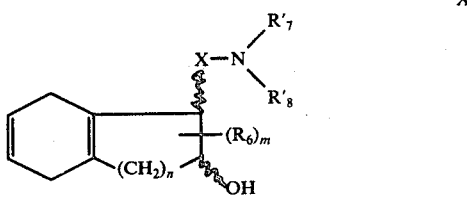

wherein $R'_7$ and $R'_8$ are the same or different and can be aryl, substituted aryl, arylalkyl, substituted arylalkyl or any of the $R_7$ and $R_8$ substitutents mentioned previously. The substituted aryl groups can include any of the substituents set out hereinbefore with respect to the heterocyclic groups. The aminoalkyl diene can be converted to the corresponding pentol by reacting the diene with formic acid and an oxidizing agent, such as hydrogen peroxide, removing solvent and subjecting the residue to basic hydrolysis (alcohol-base) as described hereinbefore, to form a pentol of the structure:

XI

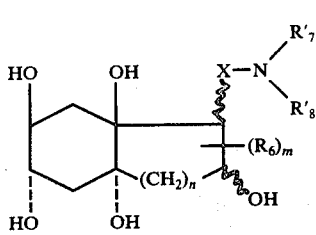

wherein $R'_7$ and $R'_8$ are as defined above. When $R'_7$ or $R'_8$ is benzyl it can be converted to a hydrogen atom by treating the pentol with hydrogen in the presence of a catalyst for reduction, such as palladium on strontium carbonate.

Where Y is $NH_2$, the pentols of the invention can be prepared by reacting an aminoalkyl indene (prepared by reduction of the corresponding cyanoalkyl indene) or an aminoalkyl tetrahydronaphthalene with a reducing agent, such as lithium ribbon in the presence of liquid ammonia, ethyl ether, and a proton source such as a lower alcohol, to form a diene of the structure:

XII

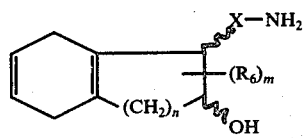

and reacting the diene with an acyl halide (wherein acyl and the halogen are as defined hereinbefore), such as benzoyl chloride, in a molar ratio of diene:halide of within the range of from about 1:1 to about 2:1 in a basic solvent, such as pyridine, triethylamine, or dilute base to form a diene of the structure

XIII

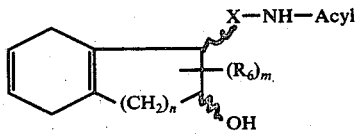

and reacting the diene with formic acid and an oxidizing agent, such as hydrogen peroxide, and subjecting the product to basic hydrolysis (as described hereinbefore) to form an aminioalkyl pentol of the structure:

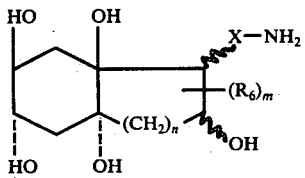

XIV

The pentol tetraacylate of formula I, wherein $R_5$ is H, can be prepared from the diene alcohol X (or II) by conversion to the succinate half ester, A, using

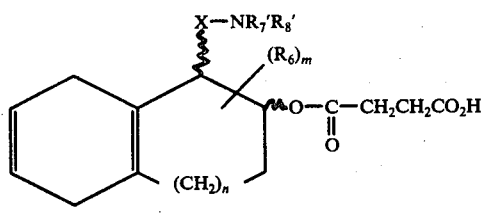

A succinic anhydride in pyridine, converting this to a salt with a strong non-participating acid, such as perchloric, in a carboxylic acid, such as acetic, oxidizing with the peracid of the same carboxylic acid, such as peracetic acid, in a ratio of peracid to diene of about 2:1 to about 3:1, precipitating the oxidation product by addition of non-polar diluents, such as benzene and ethyl ether, and acylating the crude oxidation product with the addition of the same carboxylic acid anhydride, such as acetic anhydride, to give, on dilution with ethyl ether, the tetra acyl succinate, B.

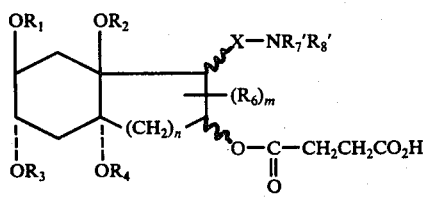

B

The tetraacyl succinate B can be converted to the pentol tetra acylate C by dissolving in an aqueous solution of

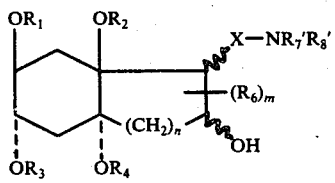

C a weak base, such as sodium bicarbonate, and warming at temperatures from 40°–80° C for a period of from 15 minutes to 1 hour.

PREPARATION OF OTHER TETROL DERIVATIVES

The pentol ethers of formula I wherein $R_1$, $R_2$, $R_3$, $R_4$ and $R_5$ are lower alkyl can be prepared by dissolving a pentol of Formula I in a suitable nonprotonic solvent such as benzene, dioxane, ethyl ether or tetrahydrofuran, adding to the solution at least four equivalents and preferably from about five to about seven equivalents of a metal hydride such as sodium hydride or sodium amide, thereafter adding to the mixture slowly with stirring about five equivalents of a lower alkyl halide such as methyl iodide, methyl bromide or ethyl iodide, and maintaining the temperature of the reaction mixture within the range of from about 20° to about 60° C and preferably from about 30 to about 40° C, to form the tetrol ether. Thereafter, ethyl alcohol and/or water can be added to decompose excess base, and the tetrol ether can be recovered by stripping down the organic solvent.

Pentols of Formula I wherein $R_1$, $R_2$, $R_3$, $R_4$ and $R_5$ are halo-lower alkyl can be formed as described hereinbefore with respect to the preparation of the pentol ethers with the exception that an alkylene halohalide (or dihaloalkane) such as trimethylene chlorobromide or pentamethylene fluoro iodide, is employed in place of the alkyl halide.

Pentols of Formula I wherein $R_1$, $R_2$, $R_3$, $R_4$ and $R_5$ are dialkyl carbamyl can be found as described hereinbefore with respect to the preparation of the pentol ethers with the exception that a dialkyl carbamoyl halide, such as dimethyl carbamyl chloride or diethyl carbamoyl bromide, or a substituted isocyanate such as an alkyl or aryl isocyanate is employed in place of the alkyl halide.

Pentols of Formula I wherein $R_1$, $R_2$, $R_3$, $R_4$ and $R_5$ are lower alkoxyalkylene wherein the alkylene group contains two to five carbon atoms can be formed as described hereinbefore with respect to the preparation of the pentol ethers except that an alkoxyalkylene halide such as ethoxypropyl chloride or ethoxyethyl bromide is employed in place of the alkyl halide.

Pentols of Formula I wherein $R_1$, $R_2$, $R_3$, $R_4$ and $R_5$ are

can be formed as described hereinbefore with respect to the preparation of the pentol ethers except that an alkylhaloformate such as methylchloroformate or ethylchloroformate is employed in place of the alkyl halide.

Alternative Methods for Preparing Indanyl, Naphthyl and Benzosuberanyl Derivatives The dienes of the structure

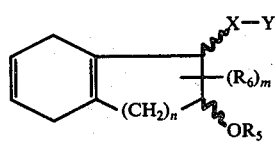

II are novel intermediates.

The triol olefins of the structure VI that is

-continued

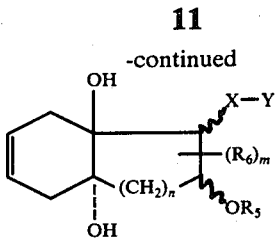

VI wherein X and Y are defined hereinbefore are novel intermediates.

Triol olefins of the structure VI correspond to the pentols and esters and the triester and triol olefins of structures IV and V set out hereinbefore.

The diene intermediate II, when n=1,

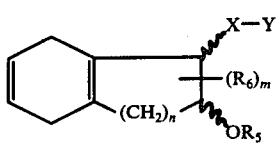

II can be prepared by reacting a starting material of the structure

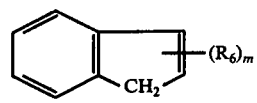

XVIII with an alkylene oxide and a strong base such as butyl-lithium or butyl-sodium in a solvent such as ethyl ether to form the hydroxyalkyl compound of the structure,

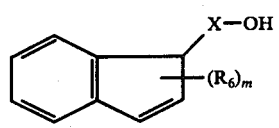

XIX dissolving the hydroxyalkyl compound in a basic organic solvent, such as pyridine, cooling the solution to below 0°, treating the solution with a solution of p-toluene sulfonyl chloride in pyridine, in a molar ratio of hydroxyalkyl compound to p-toluene sulfonyl chloride of within the range of from about 1:1 to about 1:1.5, and cooling to form the corresponding tosylate of the structure,

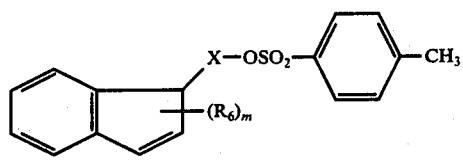

XX reacting the tosylate with an amine of the structure

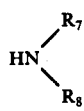

in a molar ratio of tosylate to amine of within the range of from about 1:2 to about 1:5, in an aromatic solvent boiling below about 120° C, such as toluene or benzene, to form an aminoalkylene compound of the structure

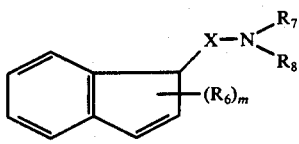

XXI

Thereafter, the aminoalkylene compound can be subjected to hydroboration of the double bond by reaction with diborane. The reaction mixture is then subjected to oxidation by treating with alkali metal hydroxide and hydrogen peroxide to form a compound of the structure

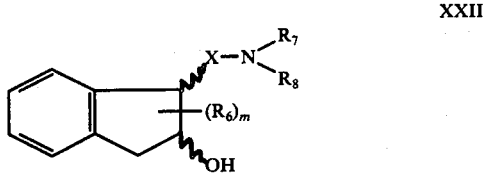

XXII which is reduced by reaction with a reducing agent, such as lithium ribbon in the presence of liquid ammonia, ethyl ether and a proton source such as a lower alcohol, to form a diene of the structure II, when n=1. Alternatively, the diene intermediate II, when n=1, can be prepared by reacting a starting material such as XVIII with an alkyl dihalide, such as 1,3-dibromo propane, and a strong base such as Triton B and a metal hydroxide, in water, to form the haloalkyl compound of the structure

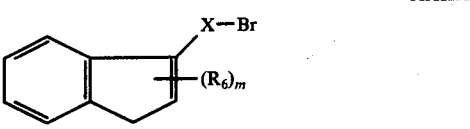

XXIIA reacting the halide with an amine of the structure

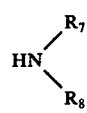

in a molar ratio of halide to amine of within the range of from about 1:2 to about 1:5, in an aromatic solvent boiling below about 120° C, such as toluene or benzene, to form an aminoalkylene compound of the structure

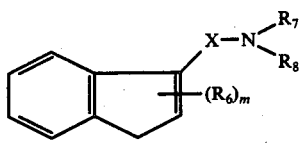

XXIIB which can be reacted as was XXI to give XXII.

The diene intermediate II, when $n=1$, 2 or 3,

-continued

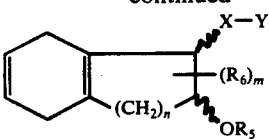
II can be prepared starting with the ketone shown below.

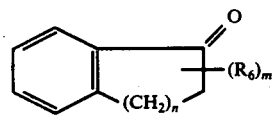
IIA

Reaction of the ketone with an aminoalkyl Grignard reagent followed by acid catalyzed dehydration yields the amino alkylene compound

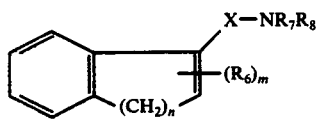
XXIII

The reaction sequence of hydroboration and oxidation with alkaline hydrogen peroxide yields the intermediate

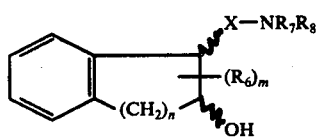
XXIV which is reduced as with XXII to the diene II.

Dienes of the structure II may alternatively be prepared by formic acid-hydrogen peroxide hydroxylation of the double bond conjugated to the aromatic ring in a compound of the structure

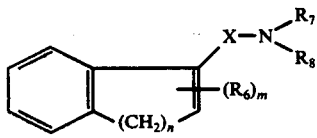
XXIII to form a diol, which on acid treatment forms the ketone.

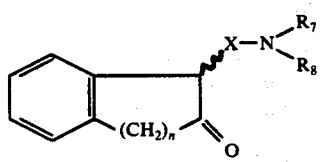
XXV

This is reduced by reaction with a complex metal hydride to form the alcohol XXIV which is reduced as above.

The following examples illustrate the present invention without, however, limiting the same thereto. All temperatures are expressed in degrees Centigrade.

EXAMPLE 1

2,3-trans-4a,8a-trans-5-[3-(Dimethylamino)propyl]-decahydro-2,3,4a,6,8a-naphthalenepentol

A. 1-Dimethylaminopropyl-3,4-dihydronaphthalene

The Grignard reagent from 300 g (2.5 moles) of dimethylaminopropyl chloride and 60 g (2.5 moles) of magnesium turnings is prepared in 2 l. of tetrahydrofuran. To this is added 300 g (2.0 moles) of α-tetralone in 1 l. of tetrahydrofuran, at a rate to maintain reflux. After the addition the reflux is continued for 1.5 hours, then the mixture is cooled in ice and quenched with 500 ml of saturated ammonium chloride. The layers are separated, and the aqueous diluted with water and reextracted with ether. The organics are evaporated, then treated with a mixture of 350 ml of concentrated HCl and 1400 ml of glacial acetic acid at reflux for ½ hour. The solvents are removed in vacuo, and the residue taken up in water, and the aqueous extracted with benzene. Basification liberates the product which is extracted with benzene, dried over carbonate, the solvent evaporated, and the product distilled at 129° C, 0.3 mmHg to give 250 g (58%) of a light yellow liquid, 1-dimethylaminopropyl-3,4-dihydronaphthalene.

B.
1,2-trans-1-[3-(Dimethylamino)propyl]-1,2,3,4,5,8-hexahydro-2-naphthol

A solution of 1-dimethylaminopropyl-3,4-dihydronaphthalene (43 g) in 300 ml of tetrahydrofuran is treated over 45 minutes with 400 ml of 1M borane solution in tetrahydrofuran at 0° C under nitrogen. The mixture is warmed to 25° C for 1 hour, then cooled to 0° C and treated with 60 ml of water by drops, 340 ml of 10% sodium hydroxide, and finally 75 ml of 30% hydrogen peroxide over 15 minutes. After stirring 1 hour at 0°-15° C the mixture is diluted to 2 liters with water, the layers separated, and the aqueous extracted with 1.5 liters of chloroform. Drying (sodium sulfate) and evaporation gives an oil which is refluxed 1 hour in a mixture of 600 ml of 95% ethanol and 600 ml of 5% HCl. Another 600 ml of water is added and ethanol evaporated in vacuo. The resulting aqueous phase is extracted with chloroform (discard), basified (10% caustic) and extracted with chloroform (1 liter). The organics are dried (sodium sulfate), 500 ml of benzene is added, and the mixture evaporated to give 43 g (93%) of the 2-hydroxy compound, largely a single spot on TLC, chloroform, neutral alumina.

The above amino alcohol (43 g, 0.18 mole) in 300 ml of ether is added to 2 liters of ammonia, treated with 35 g (5 moles) of lithium, stirred 1 hour, and treated with absolute ethanol over 3 hours to discharge the blue color. The ammonia is evaporated overnight, and water and ether are added with ice cooling. The aqueous phase is reextracted with ether, the organics dried (potassium carbonate), benzene added, and evaporated to give 38 g (87%) of 1,2-trans-1-[(dimethylamino)propyl[-1,2,3,4,5,8-hexahydro-2-naphthol.

C.
2,3-trans-4a,8a-trans-5-[3-(Dimethylamino)propyl]-decahydro-2,3,4a,6,8a-naphthalenepentol A solution of 33 g (0.14 mole) of the free base formed in part B in 1 liter of 88% formic acid is treated over 5 minutes with 40 ml (0.35 mole) of 30% hydrogen peroxide, T ≧ 38° C with cooling. After 3½ days at room temperature the mixture is evaporated to an oil, taken up in 500 ml of 95% ethanol, basified with 10% sodium hydroxide and heated for 1 hour on a steam cone. Cooling, extraction with ether and ethyl acetate until the organics are colorless, drying (magnesium sulfate) and evaporation with added benzene gives 27 g of an oil. This is taken up in 300 ml of acetonitrile and 100 ml of ethyl acetate, and diluted while hot with 600 ml of benzene. Cooling and occasional scratching give after two days 9.0 g (21%) of crude 2,3-trans-4a,8a-trans-5-[3-(dimethylamino)propyl]-decahydro-2,3,4a,6,8a-naphthalenepentol, m.p. 123°–129° C.

A 1.7 g sample of pentol is crystallized after Darco treatment from 60 ml of ethyl acetate. The crystals are crushed and dried at 80° C over $P_2O_5$ and paraffin at 0.1 mm Hg for two days to give 1.2 g, m.p. 140°–143° C.

EXAMPLE 2

2,3-trans-4a,8a-trans-5-[3-(Dimethylamino)propyl]-decahydro-2,3,4a,6,8a-naphthalenepentol, pentaacetate ester A 3.0 g (0.01 mole) sample of 2,3-trans-4a,8a-trans-5-[3-(dimethylamino)propyl]-decahydro-2,3,4a,6,8a-naphthalenepentol (prepared as in Example 1) is slurried in 100 ml of acetic anhydride, cooled in a Dry Ice-acetone bath and treated with 3 ml of 70% perchloric acid. After standing at −15° C overnight the mixture is cooled in ice-acetone and treated dropwise with 70 ml of methanol. The solution is poured into a mixture of ice and concentrated ammonium hydroxide, extracted with ether and chloroform, the combined extracts dried (magnesium sulfate) and evaporated with added benzene to give 4.6 g (90%) crude solid 2,3-trans-4a,8a-naphthalenepentol, pentaacetate ester.

Recrystallization from 225 ml of 2:1 hexane:ethyl acetate with Darco treatment and drying for 24 hours at 140° C over $P_2O_5$ and paraffin at 0.1 mm Hg give 1.8 g, m.p. 201°–206° C.

EXAMPLE 3

2,3-trans-4a,8a-trans-5-[3-(Dimethylamino)propyl]-decahydro-2,3,4a,6,8a-naphthalenepentol, pentaacetate ester (Isomer of the product of Example 2)

A 30.4 g (0.14 mole) sample of 1-(3-dimethylaminopropyl)-3,4-dihydronaphthalene (prepared as in Example 1A) is taken up in 350 ml of 97% formic acid and treated while still warm with 13.2 ml of 30% hydrogen peroxide, T ≦ 50° C, with cooling. After standing overnight the mixture is stripped to an oil, then taken up in 300 ml of 5% sulfuric acid and heated on a steam cone for 1 hour. The mixture is cooled, basified with 10% sodium hydroxide and extracted with chloroform, the organics dried overnight at 5° C over sodium sulfate. Evaporation affords 16 g (44%) of crude product. This is taken up in 300 ml of dichloromethane and added to a slurry of 14 g of lithium aluminum hydride in 400 ml of ether. This mixture is refluxed 1 hour, then quenched with ethyl acetate and finally water. Filtration and evaporation affords 9 g (59%) oily product. This material (0.036 mole) is submitted to Birch reduction using 10 g (1.5 mole) lithium, 500 ml of ammonia and 100 ml of ether to give 4.5 g (56%) of oily hydroxydiene. This material (0.02 mole) is oxidized with 10 ml of 30% hydrogen peroxide in 200 ml of 97% formic acid. After 18 hours, the mixture is stripped, hydrolyzed in ethanolic sodium hydroxide, extracted with ethyl acetate, dried (magnesium sulfate) and stripped to an oil with benzene added to remove water. The oil is triturated with hexane, and the residue taken up in 100 ml of acetic anhydride and 10 ml of acetic acid, and the peracetylation at −15° C catalyzed with 3.5 ml of 70% perchloric acid. Workup, by using 70 ml of methanol gives an oil showing very weak hydroxyl absorption in the infrared spectrum. This is boiled in 50 ml of hexane until no more dissolved. Decanting and cooling overnight gives 2 g (20%) of crude pentaacetate. This is taken up in dihloromethane (40 ml), hexane added and boiled until the dichloromethane is removed (volume = 100 ml). Standing at room temperature overnight gives 0.4 g, m.p. 178°–195° C. The mother liquor is concentrated on a steam cone to 40 ml, cooled to 25° C and scratched. Filtering in 3 hours gives 0.6 g of 2,3-trans-4a,8a-trans-5-[3-(dimethylamino)propyl]decahyro-2,3,4a,6,8a-naphthalenepentol, pentaacetate ester, m.p. 156°–163° C.

EXAMPLE 4

3a,7a-trans-5,6-trans-1-[3-(Dimethylamino)propyl]hexahydro2,3a,5,6,7a-indanpentol A. trans-1-[3-(Dimethylamino)propyl]-2-indanol A solution of 20.6 g (0.10 mole) of 1-[3-(dimethylamino)-propyl]-indene in 100 ml of tetrahydrofuran is coold to 0° under nitrogen and 200 ml of 1M borane in tetrahydrofuran added over 30 minutes. After stirring overnight at ambient temperature the solution is cooled to 0° and the following added in the given order: 30 ml of water added cautiously, 170 ml of 10% sodium hydroxide solution and 32 ml of 30% hydrogen peroxide solution. After 1 hour at 0° the mixture is diluted with 1 liter of water and extracted with chloroform (3 × 400 ml) to give a white solid which is refluxed with 300 ml each of ethanol and 5% hydrochloric acid for 1 hour. After addition of 300 ml of water, 400 ml of distillate is collected. The residue is cooled, extracted with chloroform (200 ml, discard), basified with excess sodium hydroxide and extracted with chloroform (3 × 300 ml). Drying and solvent removal give 17.6 g of oil (81%, 1 spot on TLC).

3a,7a-trans-5,6-trans-1-[3-(Dimethylamino)propyl]-hexahydro-2,3a,5,6,7a-indanpentol, hydrochloride trans-1-[3-(Dimethylamino)propyl]-2-indanol (13.9 g, 0.054 mole) is dissolved in a mixture of 100 ml of tetrahydrofuran and 1 liter of liquid ammonia. Over 40 minutes, 17.5 g (2.5 g-atom) of lithium is added followed by 220 ml of ethanol over 195 minutes. The ammonia is evaporated and the residue poured into 1 liter of ice-water and extracted with chloroform (3 × 500 ml). Drying and solvent removal gives 13.1 g of oil with negligible UV absorption at 250–300 M$\mu$ (2.2 × 10$^{-3}$M).

This oil is dissolved in 130 ml of cold 98% formic acid and the temperature brought to 24°. Over 10 minutes, 12 ml of 30% hydrogen peroxide is added and the temperature kept at 40° with a cold water bath. After 30 minutes the temperature begins to fall and the mixture is stirred for 3 days at ambient temperature. The formic acid is removed in vacuo and the residue refluxed for 1 hour with 100 ml of ethanol, 100 ml of water and 30 g of sodium hydroxide. After cooling, the mixture is extracted with ether (8 × 150 ml) and chloroform-methanol (19:1) to give 3.1 and 0.4 g of dark oil, respectively. (TLC shows 5 major components).

The aqueous solution is diluted with water, concentrated to 150 ml and the sodium hydroxide neutralized by passing gaseous carbon dioxide through the solution. A dark oil forms which is mechanically separated, taken up in 5% methanol in chloroform, dried over magnesium sulfate and evaporated to give 5.3 g of heavy oil which resists crystallization. Conversion to the hydrochloride and recrystallization three times from isopropanol give 1.65 g, m.p. 190°-195° dec.

The mother liquors are combined and the volume reduced to give, in two crops, 1.50 g of tan powder, m.p. 179°-185° dec.

EXAMPLE 5

3a,7a-trans-5,6-trans-1-[3-(dimethylamino)propyl]hexahydro2,3a,5,6,7a-indanpentol, pentaacetate ester A slurry of 1.50 g (0.0046 mole) of 3a,7a-trans-5,6-trans-1-[3-(dimethylamino)propyl]-hexahydro-2,3a,5,6,-7a-indanpentol (prepared as in Example 4) in 60 ml of acetic anhydride is cooled to dry ice-acetone temperature and 1.0 ml of 70% perchloric acid added. The solid dissolves as the temperature is raised to −20°. After storing overnight at −15°, 30 ml of methanol is added at <−10°, and the resulting solution partitioned between 100 ml of cold concentrated ammonium hydroxide and 200 ml of ether. The ether layer is separated, washed with water, saturated salt solution and dried. Solvent removal gives 1.83 g of oil which solidifies and is recrystallized twice from ca. 8/2 - hexane/ethyl acetate to give 1.19 g, m.p. 137.5°-145.5°.

EXAMPLE 6

1,2-trans-3a,7a-trans-5,6-trans-Hexahydro-1-(2-piperidinoethyl)-2,3a,5,6,7a-indanpentol

A. 2-(1-Indenyl)ethanol

The above compound is prepared as described by Howell & Taylor, J.C.S., 1957, 3013. To butyl-lithium, prepared from lithium (20.0 g) and butyl bromide (234 g) in ether, indene (116 g., 1.0 M) is added with stirring under nitrogen at −10°. After 1 hour at −10°, ethylene oxide (88 g) in ether (300 ml) is added in ½ hour. After warming to 10°, 500 ml water is added cautiously and stirring is continued until there is no lithium remaining. The layers are separated and the organic layer is washed once with dilute HCl and three times with water. After drying the ether is removed and the product distilled - collecting 76 g (48%) at 125-135/0.2 mm. N.M.R. establishes the position of the double bond as 2,3.

B. 2-(1-Indenyl)ethyl tosylate

The alcohol prepared as described above in part A (49 g, 0.306 M) is mixed with 64.8 g (0.350 M) p-toluenesulfonyl chloride. The paste is cooled to 0° and pyridine (49 g, 0.62 M) is added dropwise over a period of one hour. The cold solution is stirred for four hours before an excess of dilute HCl is added. The product is extracted with ether yielding 95 g (99+%) viscous tosylate. N.M.R. establishes the position of the double bond as 2,3.

C. 1-[2-(3-Indenyl)ethyl]piperidine

The crude tosylate prepared as described in part B above (41.5 g, 0.13 M) and piperidine (28 g, 0.33 M) in 200 ml toluene are heated under reflux overnight. Ether is added to the warm reaction mixture until crystals begin forming. After cooling, the solid is removed by filtration and washed several times with ether. The filtrate and washes are combined and the solvents removed in vacuo. The oily residue is dissolved in ether, a small amount of insoluble material is removed by filtration, and the ether is removed from the filtrate leaving 29.7 g (99%) of brown oil. The sample is purified by distillation at reduced pressure recovering 86% as a yellow oil boiling 115°/0.05 mm. to 130°/0.1 mm.

D. 1-(2-Piperidinoethyl)-2-indanol

The 1-[2-(3-indenyl)ethyl]piperidine compound prepared as described above in part C is hydroborated with diborane generated in situ. The indenyl compound (20.4 g, 0.09 M) and sodium borohydride (9.0 g, 0.22 M) are dissolved in 300 ml of diglyme which has been purified by distillation from lithium aluminum hydride. The system is swept with nitrogen and cooled in an ice bath. A solution of boron trifluoride etherate (50.4 g, 0.36 M) in diglyme (60 ml) is added dropwise over a period of one hour, maintaining the temperature at 5°-7° C. This temperature is held 1 hour after addition then left 2 hours at room temperature.

The excess hydride is decomposed by cautious addition of 20 ml water. The mixture is then oxidized by addition of 75 ml of 6 N NaOH and dropwise addition (1 hour) of 150 ml 30% hydrogen peroxide. Two hours after addition is complete the mixture is filtered, acidified with dilute HCl, and the solvent is removed in vacuo heating to ∼ 70° C. The yellow solid which remains is dissolved in water, basified with solid $K_2CO_3$, and the product is extracted with benzene giving 18.5 g crude alcohol. This is dissolved in ether, converted to the hydrochloride which is filtered off (16.3 g, 64%, melting 197°-200°).

The hydrochloride is dissolved in water, basified with NaOH and the free base is extracted with ether. After removal of the ether 13.1 g of oil remains (60%).

E. 1,2-trans-3a,7a-trans-5,6-trans-Hexahydro-1-(2-piperidinoethyl)-2,3a,5,6,7a-indanpentol A solution of the 1-(2-piperidinoethyl)-2-indanol prepared as described above in part D (13.1 g, 0.053 M) in 100 ml ether is added to 1 l. liquid ammonia and 100 ml ether. Lithium ribbon (20.0 g, 2.85 M) is added in several portions over a period of 15 minutes while stirring. The bluish-bronze mixture is stirred 1½ hours. Absolute ethanol is added dropwise until the blue color is discharged (300 ml is required, added over a period of 2 hours). The ammonia is evaporated, the residue is diluted to 1500 ml with water and extracted three times with ether. The ether extracts are dried over magnesium sulfate and the ether is removed in vacuo leaving 13.5 g amber oil. Comparison of the IR and UV of the product with those of the starting material indicates no starting material remains.

The oil (0.053 M) is added dropwise over a period of 15 minutes to 100 ml cold 98% formic acid. This is followed by dropwise addition (30 minutes) of 57 g (∼ 0.5 M) 30% hydrogen peroxide maintaining a temperature of 20° C. The temperature is then allowed to rise to 35° and is held at 30°-35°, using a large water bath, for three hours before it is left stirring overnight. The reaction mixture is taken to near dryness and any residual performic acid is removed by twice adding water and removing in vacuo.

The remaining yellow oil is dissolved in 100 ml absolute ethanol. A solution of 30 g KOH in 50 ml water is added. The mixture, which darkens immediately, is heated under reflux one hour. After cooling, the mixture is diluted to 500 ml with water. This is extracted three times with ether (yield: 3.4 g), two times with chloroform (yield: 2.4 g) and finally three times with i-amyl alcohol (yield: 8.0 g). Total material extracted: 13.8 g (77%). The extracts are crystallized separately from methanolacetone. First crop materials (3.5 g combined) have similar melting points and identical IR's. They are combined and purified by recrystallization from methanolacetone to give 2.2 g (12%) m.p. 223°–226° C.

EXAMPLE 7

3a,7a-trans-5,6-trans-Hexahydro-1-(3-piperidinopropyl)-2,3a,5,6,7a-indanpentol, hydrochloride

A. 3-(3'-Bromopropyl)indene

The compound is prepared as described by Makoska in Tetrahedron Letters 38, 4261–4624 (1966) by adding a mixture of 580 g (5M) indene and 1010 g (5M) 1,3-dibromopropane to 1500 ml 50% aqueous NaOH containing 50 ml 40% methanolic Triton B. The temperature is held below 55° C by cooling in an ice bath. After stirring 6 hours the reaction mixture is diluted to 4 l. The layers are separated and the aqueous layer is extracted two times with ether. The combined organic layers are extracted two times with water, dried over $MgSO_4$, filtered and the solvent is removed. The oily product is distilled and redistilled at reduced pressure collecting 432 g (36.6%) boiling 126°–140°/0.1 mm.

B. 1-[3-(3-Indenyl)propyl]piperidine 3-(3'-Bromopropyl)indene (94.8 g, 0.4 M) and piperidine (76 g, 0.9 M) are dissolved in 400 ml toluene. The mixture is heated under reflux 2 hours. After cooling, a large amount of solid is removed by filtration and washed with ether. The combined filtrate and washes are concentrated in vacuo. The residue is dissolved in ether and filtered to remove a small amount of insoluble material. The ether is removed in vacuo and the product is distilled collecting a fraction of 87.3 g (89% yield) boiling 132°–153°/0.05 mm.

C. 1-(3-Piperidinopropyl)-2-indanol

1-[3-(3-Indenyl)propyl]piperidine (48.2 g, 0.2 M) is dissolved in 400 ml tetrahydrofuran and stirred in a nitrogen atmosphere while 400 ml 1M borane in tetrahydrofuran is added dropwise over a period of 1 hour. The mixture is left stirring overnight at room temperature. Most of the solvent is then removed in vacuo. The viscous residue is dissolved in 500 ml 95% ethanol, treated with 20 g NaOH and then 65 ml of 30% $H_2O_2$ is added dropwise over a period of 30 minutes. The mixture is stirred at room temperature for 2 hours and then heated under reflux for 2½ hours. The mixture is then taken to near dryness in vacuo. The residue is then extracted three times with benzene. The benzene extracts are dried, filtered and the solvent is removed in vacuo leaving 57 g of oil. The VPC of this material indicates ~ 97% purity.

D. 4,7-Dihydro-1-(3-piperidinopropyl)-2-indanol

The crude 1-(3-piperidinopropyl)-2-indanol (~ 0.2 M) is dissolved in 300 ml ether and added to 2 liters liquid ammonia. Lithium ribbon (50 g) is added in small portions over a period of 30 minutes. After stirring 1½ hours, absolute ethanol is added dropwise until the color is discharged (~ 1 liter added over a period of 4 hours). The ammonia is allowed to evaporate and the residue is then diluted to 4 liters with water; two ether extracts yield 62 g of crude diene which becomes partially crystalline on standing.

E. 3a,7a-trans-5,6-trans-Hexahydro-1-(3-piperidinopropyl)-2,3a,5,6,7a-indanpentol, hydrochloride Crude 4,7-dihydro-1-(3-piperidinopropyl)-2-indanol (prepared as described in part C) (~ 0.19 M) is added slowly to 300 ml cold 98% formic acid. Hydrogen peroxide (175 ml of 30%) is then added dropwise over a period of 45 minutes maintaining a temperature of 20°–25° C. The temperature is then allowed to rise to 35° and is held at 30°–35°, using a large water bath, for three hours before the mixture is left stirring overnight. Water (50 ml) is added and excess peroxide is decomposed by adding sodium sulfite. The solvent is removed in vacuo.

The viscous residue is dissolved in 400 ml 95% ethanol and treated with a solution of 90 g KOH in 100 ml water. The dark mixture is heated under reflux 1 hour, cooled, and diluted to 1 liter with water. Four ether extracts yield 41.4 g and four ethyl acetate extractions yield an additional 9.3 g. Only 2 g is obtained partially crystalline (this from ethyl acetate extracts). The remaining material is chromatographed on Activity IV basic alumina. Elution with 5 and 10% methanol in chloroform give fractions containing 29.4 g of material. This material is dissolved in ethyl acetate and after standing 15.9 g of crude 3a,7a-trans-5,6-trans-hexahydro-1-(3-piperidinopropyl)-2,3a,5,6,7a-indanpentol is removed by filtration (total solid 17.9 g, 29% yield).

A 4 g sample of the crude pentol is converted to the hydrochloride by reacting the same with hydrochloric acid. Three recrystallization from isopropyl alcohol-ethanol yield 1.5 g (~ 34%), m.p. 215° (dec).

EXAMPLE 8

3a,7a-trans-5,6-trans-Hexahydro-1-(3-piperidinopropyl)-2,3a,5,6,7a-indanpentol, pentaacetate ester Crude 3a,7a-trans-5,6-trans-hexahydro-1-(3-piperidinopropyl)-2,3a,5,6,7a-indanpentol (3.0 g, 0.0091M) (prepared as described in Example 7) is partially dissolved in 60 ml acetic anhydride and 2 ml acetic acid. While cooling to −30° C, 4.5 ml 70% $HClO_4$ dropwise is added over a period of 15 minutes. The mixture is kept at −15° for 22 hours; solid precipitates during this time. Cooling is continued during dropwise addition of methanol (30 ml); the mixture is then poured into 100 ml cold concentrated $NH_4OH$, and extracted two times with chloroform. The chloroform extract are dried over $MgSO_4$, filtered, and the solvent is removed in vacuo leaving 5.28 g of yellow foam. Two recrystallizations from hexane containing a small amount of ether yield 3.7 g (76%) m.p. 121°–140° C.

EXAMPLE 9

3a,7a-trans-5,6-trans-Hexahydro-1-[3-(trans-3-hydroxy-4-methylpiperidino)propyl]-2,3a,5,6,7a-indanpentol, hydrochloride

A. 1-[3-(3-Indenyl)propyl]-4-methylpyridinium bromide

A solution of 121 g (0.51 mole) of 3-(3-bromopropyl)indene (prepared as in Example 7) and 68 g (0.74 mole) of γ-picoline in 150 ml of acetonitrile is heated at reflux temperature overnight. A small amount of ether is added and the mixture let stand at room temperature for 3 hours, and then filtered. The solid collected is washed with ether and dried in vacuo to give 138 g (0.419 mole) of tan solid, mp 93°–123°.

B.
1,2,3,6-Tetrahydro-1-[3-(3-indenyl)propyl]-4-methylpyridine, hydrochloride A solution of 135 g (0.409 mole) of the compound formed in part A above in 200 ml of water and 120 ml of methanol is cooled to 15°. Over a period of 30 minutes, 16 g (0.424 mole) of sodium borohydride is added. The mixture is stirred for 2 hours at room temperature, acidified with glacial acetic acid, and then basified with potassium carbonate. It is extracted with a total of 1200 ml of ethyl ether (containing 200 ml of chloroform) and 600 ml of chloroform. All organic extracts are combined, dried and evaporated in vacuo to give 129 g of an orange-brown liquid.

A chloroform solution of this material is extracted with 1 liter of 7% hydrochloric acid which is separated, basified and extracted with ether. The ether extract is dried and evaporated to give 19 g of black sludge which is discarded. The original chloroform layer is evaporated in vacuo to give 140 g of dense oil whose IR spectrum indicates that it is a hydrochloride salt. This material is slurried with ether, basified and the ether layer dried and evaporated to give 82 g of mobile oil which is distilled in vacuo to give, after a forerun of 5.7 g, bp 130–151° at 0.4 mm, 41.3 g of oil, bp 146–156° at 0.4 mm.

C.
trans,trans-1-[3-(3-Hydroxy-4-methylpiperidino)propyl]-2-indanol, hydrochloride A solution of 41.26 g (0.16 mole) of 1,2,3,6-tetrahydro-1-[3-(3-indenyl)propyl]-4-methylpyridine (as the free base) in 350 ml of tetrahydrofuran is cooled to 10°, and 340 ml of 7M borane in tetrahydrofuran (0.34 mole) is added over 25 minutes. The mixture is stirred overnight at room temperature, cooled to 0° and 40 ml of water is added carefully. A solution of 30 g of sodium hydroxide in 270 ml of H$_2$O is added followed by 70 ml of 30% hydrogen peroxide over 25 minutes. The mixture is stirred at room temperature for 1 hour and then the layers separated. The aqueous phase is washed twice with ether, and then all organic extracts are combined, washed with saturated sodium chloride solution, dried over sodium sulfate and evaporated in vacuo to give 62 g of dense oil. This is dissolved in a solution of 100 ml of concentrated hydrochloric acid, 500 ml of ethanol and 400 ml of water and the mixture refluxed for 1 hour. Approximately 500 ml of solvent is distilled out and the remaining solution is cooled and extracted with chloroform (discard). The aqueous layer is separated, basified and then extracted with a total of 1 liter of chloroform which is dried and evaporated in vacuo to give 53.2 g of dense oil having the above name.

D.
trans-4,7-Dihydro-1-[3-(trans-3-hydroxy-4-methylpiperidino)propyl]-2-indanol A solution of 44 g (0.15 mole) of trans,trans-1-[3-hydroxy-4-methylpiperidino)propyl]-2-indanol (prepared as described in part D) (as the free base) in 150 ml of ether, 100 ml of tetrahydrofuran and ca. 1.5 l of liquid ammonia is prepared and 26.8 g (3.84 g-atoms) of lithium added over 70 minutes. The mixture is stirred at reflux for 30 minutes, 260 ml of absolute ethanol is added over 45 minutes, and the ammonia evaporated. The residue is partitioned between 900 ml of cold water and 600 ml of ether. The aqueous layer is washed with 2 × 300 ml of ether. The ether extracts are combined, washed with saturated sodium chloride solution, dried and evaporated in vacuo to give 45.2 g of dense oil (100%).

E.
3a,7a-trans-5,6-trans-Hexahydro-1-[3-(trans-3-hydroxy-4-methylpiperidino)propyl]-2,3a,5,6,7a-indanpentol, hydrochloride An amount of 38 ml of 30% hydrogen peroxide is added over 45 minutes to a solution of 45 g of trans-4,7-dihydro-1-[3-(trans-3-hydroxy-4-methylpiperidino)-propyl]-2-indanol prepared as in part B) in 400 ml of 98% formic acid. The mixture is stirred at room temperature for 64 hours, diluted with water and evaporated in vacuo twice to give an oil which is refluxed with 150 ml of 95% ethanol, 84 g potassium hydroxide and 350 ml of water for 1.5 hour. The mixture is cooled and extracted with 5% methanol in chloroform to give 8.3 g of foam (15.2%) which by TLC contains hexol contaminated by several impurities. The aqueous layer is extracted with a total of 3.2 liters of ethyl acetate to give 9.05 g of solid (16.6%). A 6.05 g portion of this solid is dissolved in isopropanol, the hydrochloride salt prepared and recrystallized twice from isopropanol/methanol/ether to a white solid, 1.3 g, m.p. 223°–224° (19.6%), and a pale yellow solid, 1.39 g (20.9%).

Example 10
3a,7a-trans-5,6-trans-Hexahydro-1-[3-(trans-3-hydroxy-4-methylpiperidino)propyl]-2,3a,5,6,7a-indanpentol, hexaacetate ester A slurry of 2 g (0.005 mole) of 3a,7a-trans-5,6-trans-hexahydro-1-[3-(trans-3-hydroxy-4-methylpiperidino)-propyl]-2,3a,5,6,7a-indanpentol (prepared as described in Example 9) in 40 ml of acetic anhydride and 1.5 ml of glacial acetic acid is cooled in a dry ice-acetone bath, 1.5 ml of 70% perchloric acid added dropwise and the solution stored 16 hours at −20°. The solution is cooled to −15°, 30 ml of methanol added and the solution poured into 100 ml of cold concentrated ammonium hydroxide. This mixture is extracted with a total of 800 ml of ether, which is washed with saturated sodium chloride, dried, and evaporated in vacuo to give 2.7 g foam (88.5%). This is recrystallized twice from hexane/ethyl acetate to give a white solid, 1.36 g m.p. 117.5°–125°.

Examples 11 to 56

Following the procedure of Example 6 but substituting for indene the compound listed in Column I of Table I set out below, and substituting for piperidine the compound listed in Column II, the compound listed in Column II is obtained.

TABLE I

| Ex. No. | Column I | | | Column II | Column III | | |
|---|---|---|---|---|---|---|---|
| | $R_6$ (position) | m | | $HN\begin{smallmatrix}R_7\\R_8\end{smallmatrix}$ | $R_6$ (position) | m | $-N\begin{smallmatrix}R_7\\R_8\end{smallmatrix}$ |
| 11. | H | — | | $HN(C_2H_5)_2$ | H | — | $-N(C_2H_5)_2$ |
| 12. | H | — | | $HN\begin{smallmatrix}CH_3\\C_2H_5\end{smallmatrix}$ | H | — | $-N\begin{smallmatrix}CH_3\\C_2H_5\end{smallmatrix}$ |
| 13. | H | — | | $NH_3$ | H | — | $NH_2$ |
| 14. | H | — | | $HNHCH_3$ | H | — | $-NHCH_3$ |
| 15. | H | — | | HN-piperazine-NH | H | — | -N-piperazine-NH |
| 16. | H | — | | morpholine (NH) | H | — | -N-morpholine |
| 17. | H | — | | thiomorpholine (HN...S) | H | — | -N-thiomorpholine-S |
| 18. | H | — | | HN-piperazine-N-CH₂CH₂OH | H | — | -N-piperazine-N-CH₂CH₂OH |
| 19. | H | — | | HN-pyrrolidine | H | — | -N-pyrrolidine |
| 20. | $C_2H_5$ (2) | 1 | | HN-piperidine | $C_2H_5$ (2) | 1 | -N-piperidine |
| 21. | $CH_3$ (1) | 1 | | HN-morpholine | $CH_3$ (1) | 1 | -N-morpholine |
| 22. | S(2) cyclohexane | 1 | | $HN(CH_3)_2$ | S(2) cyclohexane | 1 | $-N(CH_3)_2$ |
| 23. | H | — | | HN-azepane | H | — | -N-azepane |
| 24. | H | — | | $HN(CH_2Cl)_2$ | H | — | $-N(CH_2Cl)_2$ |
| 25. | H | — | | HNHN-piperazine-NH | H | — | $-NHN$-piperazine-NH |
| 26. | H | — | | HN(thianyl)(thianyl) | H | — | -N(thianyl)(thianyl) |

TABLE I-continued

| Ex. No. | Column I | | | Column II | Column III | | |
|---|---|---|---|---|---|---|---|
| | R₆ (position) | m | HN(R₇)(R₈) | | R₆ (position) | m | -N(R₇)(R₈) |
| 27. | di-CH$_3$ (1,2) | 2 | HN(CH$_2$-cyclohexyl)$_2$ | | di-CH$_3$ (1,2) | 2 | -N(CH$_2$-cyclohexyl)$_2$ |
| 28. | C$_3$H$_7$ (3) | 1 | HN(C$_6$H$_5$)$_2$ | | C$_3$H$_7$ (3) | 1 | -N(C$_6$H$_5$)$_2$ |
| 29. | H | — | HN(COCH$_3$)$_2$ | | H | — | -N(COCH$_3$)$_2$ |
| 30. | H | — | HN(CH$_2$C$_6$H$_5$)$_2$ | | H | — | -N(CH$_2$C$_6$H$_5$)$_2$ |
| 31. | CH$_3$ (2), C$_2$H$_5$ (3) | 2 | HN(piperazine-NH)$_2$ | | CH$_3$ (2), C$_2$H$_5$ (3) | 2 | -N(piperazine-NH)$_2$ |
| 32. | H | — | HN(CH$_2$CH$_2$OH)$_2$ | | H | — | -N(CH$_2$CH$_2$OH)$_2$ |
| 33. | H | — | HNHCH$_2$-cyclohexyl | | H | — | -NHCH$_2$-cyclohexyl |
| 34. | H | — | HN(C$_2$H$_5$)$_2$ | | H | — | -N(C$_2$H$_5$)$_2$ |
| 35. | H | — | HN(CH$_3$)(C$_2$H$_5$) | | H | — | -N(CH$_3$)(C$_2$H$_5$) |
| 36. | H | — | NH$_3$ | | H | — | -NH$_2$ |
| 37. | H | — | HNHCH$_3$ | | H | — | -NHCH$_3$ |
| 38. | C$_2$H$_5$ (1) | 1 | piperazine (HN-NH) | | C$_2$H$_5$ (1) | 1 | -N-piperazine-NH |
| 39. | H | — | morpholine (HN-O) | | H | — | -N-morpholine |
| 40. | CH$_3$ (2) | 1 | thiomorpholine (HN-S) | | CH$_3$ (2) | 1 | -N-thiomorpholine |
| 41. | H | — | HN-piperazine-N-CH$_2$CH$_2$OH | | H | — | -N-piperazine-N-CH$_2$CH$_2$OH |
| 42. | di-C$_2$H$_5$ (1,2) | 2 | pyrrolidine (HN) | | di-C$_2$H$_5$ (1,2) | 2 | -N-pyrrolidine |
| 43. | C$_2$H$_5$ (2) | 1 | piperidine (HN) | | C$_2$H$_5$ (2) | 1 | -N-piperidine |

TABLE I-continued

| Ex. No. | Column I | | | Column II | Column III | | |
|---|---|---|---|---|---|---|---|
| | $R_6$ (position) | m | | $HN\begin{smallmatrix}R_7\\R_8\end{smallmatrix}$ | $R_6$ (position) | m | $-N\begin{smallmatrix}R_7\\R_8\end{smallmatrix}$ |
| 44. | $CH_3$ (1) | 1 | | HN–morpholine | $CH_3$ (1) | 1 | –N–morpholine |
| 45. | thiacyclohexane (2) | 1 | | $HN(CH_3)_2$ | thiacyclohexane (2) | 1 | $-N(CH_3)_2$ |
| 46. | H | — | | HN–azepane | H | — | –N–azepane |
| 47. | H | — | | $HN(CH_2Cl)_2$ | H | — | $-N(CH_2Cl)_2$ |
| 48. | H | — | | $HNHN\!\!-\!\!piperazine\!\!-\!\!NH$ | H | — | $-NHN\!\!-\!\!piperazine\!\!-\!\!NH$ |
| 49. | H | — | | $HN(thiacyclohexyl)_2$ | H | — | $-N(thiacyclohexyl)_2$ |
| 50. | $CH_3$ (2) | 1 | | $HN(CH_2\text{-thiacyclohexyl})_2$ | $CH_3$ (2) | 1 | $-N(CH_2\text{-thiacyclohexyl})_2$ |
| 51. | $C_3H_7$ (3) | 1 | | $HN(C_6H_5)_2$ | $C_3H_7$ (3) | 1 | $-N(C_6H_5)_2$ |
| 52. | H | — | | $HN(COCH_3)_2$ | H | — | $-N(COCH_3)_2$ |
| 53. | H | — | | $HN(CH_2C_6H_5)_2$ | H | — | $-N(CH_2C_6H_5)_2$ |
| 54. | H | — | | $HN(N\!\!-\!\!piperazine\!\!-\!\!NH)_2$ | H | — | $-N(N\!\!-\!\!piperazine\!\!-\!\!NH)_2$ |
| 55. | H | — | | $HN(CH_2CH_2OH)_2$ | H | — | $-N(CH_2CH_2OH)_2$ |
| 56. | H | — | | $HNHCH_2\text{-thiacyclohexyl}$ | H | — | $-NHCH_2\text{-thiacyclohexyl}$ |

Examples 57 to 102

Following the procedure of Example 8, but substituting for the 3a,7a-trans-5,6-trans-hexahydro-1-(3-piperidinopropyl)-2,3a,5,6,7a-indanpentol the compound listed in Column III or Table I of Examples 11 to 56, the pentaacetate ester of such compounds of Examples 11 to 56 is formed.

Examples 103 to 156

Following the procedure of Example 1 but substituting for the 1-dimethylaminopropyl-3,4-dihydronaphthalene the compound set out in column I of Table II below, the compound set out in column II is obtained.

TABLE II

| Ex. No. | Column I R$_6$ (position) | m | X—Y | Column II R$_6$ (position) | m | X—Y |
|---|---|---|---|---|---|---|
| 103. | H | — | N(CH$_3$)$_2$ | H | — | N(CH$_3$)$_2$ |
| 104. | H | — | (piperidine) | H | — | (piperidine) |
| 105. | H | — | (CH$_2$)$_4$N(CH$_3$)(C$_2$H$_5$) | H | — | (CH$_2$)$_4$N(CH$_3$)(C$_2$H$_5$) |
| 106. | CH$_3$ (2) | 1 | (CH$_2$)$_3$NHC$_4$H$_9$ | CH$_3$ (2) | 1 | (CH$_2$)$_3$NHC$_4$H$_9$ |
| 107. | S (1) | 1 | (CH$_2$)$_5$N (pyrrolidine) | S (1) | 1 | (CH$_2$)$_5$N (pyrrolidine) |
| 108. | CH$_3$ (1), C$_2$H$_5$ (2) | 2 | (CH$_2$)$_6$N (morpholine) | CH$_3$ (1), C$_2$H$_5$ (2) | 2 | (CH$_2$)$_6$N (morpholine) |
| 109. | H | — | (CH$_2$)$_3$N(CH$_2$CH$_2$Br)$_2$ | H | — | (CH$_2$)$_3$N(CH$_2$CH$_2$Br)$_2$ |
| 110. | H | — | (CH$_2$)$_4$N(CH$_2$CH$_2$OH)$_2$ | H | — | (CH$_2$)$_4$N(CH$_2$CH$_2$OH)$_2$ |
| 111. | H | — | (CH$_2$)$_5$N(C$_6$H$_5$)$_2$ | H | — | (CH$_2$)$_5$N(C$_6$H$_5$)$_2$ |
| 112. | H | — | (CH$_2$)$_3$NH(piperazine-NH) | H | — | (CH$_2$)$_3$NH(piperazine-NH) |
| 113. | H | — | (CH$_2$)$_4$N(CH$_2$C$_6$H$_5$)$_2$ | H | — | (CH$_2$)$_4$N(CH$_2$C$_6$H$_5$)$_2$ |
| 114. | C$_4$H$_9$ (2) | 1 | (CH$_2$)$_7$NH$_2$ | C$_4$H$_9$ (2) | 1 | (CH$_2$)$_7$NH$_2$ |
| 115. | CH$_3$ (1) | 1 | (CH$_2$)$_3$N(thiacyclohexyl)$_2$ | CH$_3$ (1) | 1 | (CH$_2$)$_3$N(thiacyclohexyl)$_2$ |
| 116. | H | — | (CH$_2$)$_4$N(piperazine)N—CH$_2$CH$_2$OH | H | — | (CH$_2$)$_4$N(piperazine)N—CH$_2$CH$_2$OH |
| 117. | H | — | (CH$_2$)$_2$N(piperidine-OCF$_3$) | H | — | (CH$_2$)$_2$N(piperidine-OCF$_3$) |
| 118. | H | — | (CH$_2$)$_2$N(piperidine-SCF$_3$) | H | — | (CH$_2$)$_2$N(piperidine-SCF$_3$) |
| 119. | H | — | (CH$_2$)$_2$N(piperidine-COCH$_3$) | H | — | (CH$_2$)$_2$N(piperidine-COCH$_3$) |
| 120. | H | — | (CH$_2$)$_4$N(thiomorpholine) | H | — | (CH$_2$)$_4$N(thiomorpholine) |

TABLE II-continued

| Ex. No. | Column I | | | Column II | | |
|---|---|---|---|---|---|---|
| | $R_6$ (position) | m | X—Y | $R_6$ (position) | m | X—Y |
| 121. | H | — | $N(CH_3)_2$ | H | — | $N(CH_3)_2$ |
| 122. | H | — | $(CH_2)_5$-piperidino-N | H | — | $(CH_2)_5$-piperidino-N |
| 123. | H | — | $(CH_2)_4N(CH_3)(C_2H_5)$ | H | — | $(CH_2)_4N(CH_3)(C_2H_5)$ |
| 124. | $CH_3$ (2) | 1 | $(CH_2)_3NHC_4H_9$ | $CH_3$ (2) | 1 | $(CH_2)_3NHC_4H_9$ |
| 125. | thiacyclohexyl (1) | 1 | $(CH_2)_5N$-pyrrolidino | thiacyclohexyl (1) | 1 | $(CH_2)_5N$-pyrrolidino |
| 126. | $CH_3$ (1), $C_2H_5$ (3) | 2 | $(CH_2)_6N$-morpholino | $CH_3$ (1), $C_2H_5$ (3) | 2 | $(CH_2)_6N$-morpholino |
| 127. | H | — | $(CH_2)_3N(CH_2CH_2Br)_2$ | H | — | $(CH_2)_3N(CH_2CH_2Br)_2$ |
| 128. | H | — | $(CH_2)_4N(CH_2CH_2OH)_2$ | H | — | $(CH_2)_4N(CH_2CH_2OH)_2$ |
| 129. | H | — | $(CH_2)_5N(C_6H_5)_2$ | H | — | $(CH_2)_5N(C_6H_5)_2$ |
| 130. | H | — | $(CH_2)_3NH(N$-piperazinyl-$NH)$ | H | — | $(CH_2)_3NH(N$-piperazinyl-$NH)$ |
| 131. | H | — | $(CH_2)_4N(CH_2C_6H_5)_2$ | H | — | $(CH_2)_4N(CH_2C_6H_5)_2$ |
| 132. | $C_4H_9$ (2) | 1 | $(CH_2)_7NH_2$ | $C_4H_9$ (2) | 1 | $(CH_2)_7NH_2$ |
| 133. | $CH_3$ (4) | 1 | $(CH_2)_3N$(di-thiacyclohexyl) | $CH_3$ (4) | 1 | $(CH_2)_3N$(di-thiacyclohexyl) |
| 134. | H | — | $(CH_2)_4N$-piperazinyl-$N$—$CH_2CH_2OH$ | H | — | $(CH_2)_4N$-piperazinyl-$N$—$CH_2CH_2OH$ |
| 135. | H | — | $(CH_2)_2N$-piperidinyl-$OCF_3$ | H | — | $(CH_2)_2N$-piperidinyl-$OCF_3$ |
| 136. | H | — | $(CH_2)_2N$-piperidinyl-$SCF_3$ | H | — | $(CH_2)_2N$-piperidinyl-$SCF_3$ |
| 137. | H | — | $(CH_2)_2N$-piperidinyl-$COCH_3$ | H | — | $(CH_2)_2N$-piperidinyl-$COCH_3$ |
| 138. | H | — | $(CH_2)_4N$-thiomorpholino | H | — | $(CH_2)_4N$-thiomorpholino |

TABLE II-continued

| Ex. No. | Column I | | | Column II | | |
|---|---|---|---|---|---|---|
| | R₆ (position) | m | X—Y | R₆ (position) | m | X—Y |
| 139. | H | — | N(CH₃)₂ | H | — | N(CH₃)₂ |
| 140. | H | — | (CH₂)₄N-piperidine | H | — | (CH₂)₄N-piperidine |
| 141. | H | — | (CH₂)₄N(CH₃)(C₂H₅) | H | — | (CH₂)₄N(CH₃)(C₂H₅) |
| 142. | CH₃ (2) | 1 | (CH₂)₃NHC₄H₉ | CH₃ (2) | 1 | (CH₂)₃NHC₄H₉ |
| 143. | S (1) [ring] | 1 | (CH₂)₅N-pyrrolidine | S (1) [ring] | 1 | (CH₂)₅N-pyrrolidine |
| 144. | CH₃ (1), C₂H₅ (2) | 2 | (CH₂)₆N-morpholine | CH₃ (1) | 2 | (CH₂)₆N-morpholine |
| 145. | H | — | (CH₂)₃N(CH₂CH₂Br)₂ | H | — | (CH₂)₃N(CH₂CH₂Br)₂ |
| 146. | H | — | (CH₂)₄N(CH₂CH₂OH)₂ | H | — | (CH₂)₄N(CH₂CH₂OH)₂ |
| 147. | H | — | (CH₂)₅N(C₆H₅)₂ | H | — | (CH₂)₅N(C₆H₅)₂ |
| 148. | H | — | (CH₂)₃NH(N-piperazine-NH) | H | — | (CH₂)₃NH(N-piperazine-NH) |
| 149. | H | — | (CH₂)₄N(CH₂C₆H₅)₂ | H | — | (CH₂)₄N(CH₂C₆H₅)₂ |
| 150. | C₄H₉ (2) | 1 | (CH₂)₇NH₂ | C₄H₉ (2) | 1 | (CH₂)₇NH₂ |
| 151. | CH₃ (4) | 1 | (CH₂)₃N(dithiane) | CH₃ (4) | 1 | (CH₂)₃N(dithiane) |
| 152. | H | — | (CH₂)₄N-piperazine-N—CH₂CH₂OH | H | — | (CH₂)₄N-piperazine-N—CH₂CH₂OH |
| 153. | H | — | (CH₂)₂N-piperidine-OCF₃ | H | — | (CH₂)₂N-piperidine-OCF₃ |
| 154. | H | — | (CH₂)₃N-piperidine-SCF₃ | H | — | (CH₂)₃N-piperidine-SCF₃ |
| 155. | H | — | (CH₂)₂N-piperidine-COCH₃ | H | — | (CH₂)₂N-piperidine-COCH₃ |
| 156. | H | — | (CH₂)₄N-thiomorpholine | H | — | (CH₂)₄N-thiomorpholine |

EXAMPLES 157 to 209

Following the procedure of Example 8, but substituting for the 3a,7a-trans-5,6-trans-hexahydro-1-(3-piperidinopropyl)-2,3a,5,6,7a-indanpentol, the compound listed in Column II of Table II of Examples 103 to 156, the pentaacetate ester of such compounds of Examples 103 to 156 is formed.

EXAMPLE 210

2,3-trans-4a,8a-trans-5[3-(Dimethylamino)propyl]-decahydro-2,3-4a,6,7a-naphthalene pentol, 2,3,4a,8a-tetraacetate A solution of 20 g of 1,2-trans-1-[3-(dimethylamino)-propyl]-1,2,3,4,5,8-hexahydro-2-naphthol (as prepared in Example 1) in 200 ml of pyridine is treated with 10 g of succinic anhydride. After standing for 1 day at 25° C, the solvent is evaporated, toluene added and evaporated, to yield the succinate half ester. This is taken up in 140 ml of glacial acetic acid and 20 ml of acetic anhydride, cooled to 10° C in ice, and treated carefully with 7 ml of 70% perchloric acid. After stirring 15 minutes, the addition of 35 ml of 40% peracetic acid is carried out over ½ hour, at 15° C. The temperature is allowed to come to 25° C for ½ hour, then the bath temperature is raised to 45° C for 1 hour. The mixture is then cooled to 5° C and diluted with 400 ml of benzene. The upper phase is discarded, and the treatment repeated twice with benzene and twice using ethyl ether. The resulting viscous oil is cooled to $-15°$ C and dissolved cautiously in 70 ml of acetic anhydride. Another ½ ml of 70% perchloric is added, and after 1 day at $-15°$ C, another 70 ml of acetic anhydride. After two more days at $-15°$ C, the mixture is diluted with 2 l. of ethyl ether and the resulting dark gum dissolved in water and rendered basic with sodium bicarbonate. This solution is extracted quickly with ethyl acetate, then the aqueous is warmed at 60°–80° C on a steam cone for 45 minutes. The resulting mixture is extracted with chloroform, dried using magnesium sulfate, and evaporated to 10 g of an oil.

Chromatography on neutral alumina, activity II, in ethyl acetate with increasing concentrations of methanol affords a fraction containing 200 mg of pure hydroxy tetraacetate, m.p. 178°–182° C.

EXAMPLE 211

2,3-trans-4a,8a-trans-5-[3-(Dimethylamino)propyl]-decahydro-2,3,4a,6,8a-naphthalene pentol, pentamethyl ether A mixture of the pentol as prepared in Example 1, 0.01 mole, in 100 ml of dimethyl formamide is treated with 0.05 mole of sodium hydride (50% dispersion in mineral oil) and heated at 40° C for ½ hours, until hydrogen evolution has ceased. To this mixture is added 0.05 mole of methyl iodide over ½ hour, maintaining the temperature at 35°–40° C. After the addition is complete, heating is continued for 2 hours, then the mixture is cooled and treated cautiously with water to decompose excess hydride. The resulting mixture is diluted with 200 ml of water and extracted with ethyl acetate. The dried organic phase is filtered and the hydrochloride salt of the pentamethyl ether precipitated by the addition of a saturated solution of hydrogen chloride in isopropanol.

EXAMPLE 212

The penta (chloro propyl) ether of the compound of Example 1 is prepared by substituting 1-bromo-3-chloropropane for methyl iodide in Example 211.

EXAMPLE 213

The penta (ethyl carbonate) of the compound of Example 1 is prepared by substituting ethyl chloro formate for methyl iodide in Example 211.

EXAMPLE 214

The penta (dimethyl carbamate) of the compound of Example 1 is prepared by substituting dimethyl carbamyl chloride for methyl iodide in Example 211.

EXAMPLE 215

The penta (ethoxy ethyl) ether of the compound of Example 1 is prepared by substituting 2-ethoxy ethyl bromide for methyl iodide in Example 211.

What is claimed is:

1. A compound of the structure

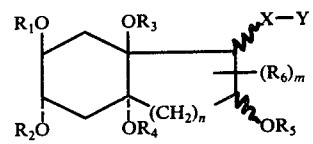

wherein $R_1$, $R_2$, $R_3$, $R_4$ and $R_5$ are the same or different and are selected from the group consisting of hydrogen, lower alkyl, trifluoromethyl, mono-halo-lower alkyl wherein the halogen is F, Cl, Br or I, acyl radical of a hydrocarbon carboxylic acid of less than 12 carbon atoms, amido, lower alkoxyalkylene and lower alkoxy carbonyl, X is a single bond or a straight or branched chain alkylene group of the structure $(CH_2)_{n'}$ wherein $n'$ is 0 to 10, Y is

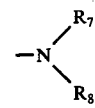

wherein $R_7$ and $R_8$ are the same or different and are selected from the group consisting of hydrogen, lower alkyl, trifluoromethyl, monocyclic cycloalkyl having 3 to 6 ring members, monocyclic cycloalkyl lower alkyl, wherein the cycloalkyl has 3 to 6 ring members, hydroxy-lower alkyl, phenyl, lower alkylphenyl, acyl radical of a hydrocarbon carboxylic acid of less than 12 carbon atoms, di(lower alkyl)phenyl, halophenyl, mono-, di- or tri-nitrophenyl, phenyl lower alkyl, monocyclic heterocyclic, wherein lower alkyl contains 1 to 8 carbons, $R_6$ is lower alkyl or cycloalkyl having 3 to 6 ring members, and

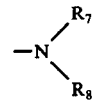

can be taken together to form a heterocyclic radical; wherein the heterocyclic radicals represented by $R_7$, $R_8$ or

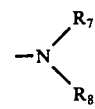

taken together contain 5-, 6- or 7-members in the heterocyclic ring, the ring being pyrrolidine, piperidine, morpholine, thiamorpholine, piperazine or homopiperazine provided that one of said rings is always present, and $n$ is 1 to 3; $m$ is 0, 1 or 2; stereoisomers thereof, physiologically acceptable acid salts thereof, physiologically acceptable quaternary salts thereof and N-oxides thereof.

2. A compound according to claim 1 wherein $R_1$, $R_2$, $R_3$, and $R_4$ are hydrogen or alkanoyl of 1 to 3 carbons.

3. A compound according to claim 2 wherein $R_1$, $R_2$, $R_3$, $R_4$ and $R_5$ are alkanoyl.

4. A compound according to claim 2 wherein $R_1$, $R_2$, $R_3$ and $R_4$ are acetyl.

5. A compond according to claim 2 wherein $R_1$, $R_2$, $R_3$, $R_4$ and $R_5$ are acetyl.

6. A compound according to claim 1 having the structure

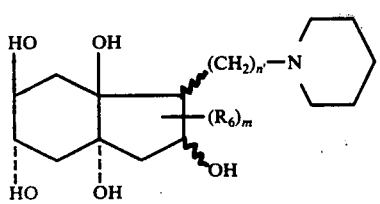

wherein $n'$ is zero to ten and $R_6$ is lower alkyl or cycloalkyl containing from 3 to 6 ring members, $m$ is 0, 1 or 2, and stereoisomers thereof.

7. A compound according to claim 1 having the structure

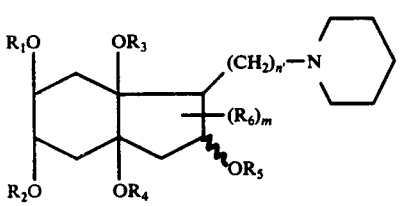

wherein $n'$ is zero to ten and $R_6$ is lower alkyl or cycloalkyl containing from 3 to 6 ring members, $m$ is 0, 1 or 2, $R_1$, $R_2$, $R_3$, $R_4$ and $R_5$ are acetyl and stereoisomers thereof.

8. A compound according to claim 1 wherein $R_1$, $R_2$, $R_3$, and $R_4$ are lower alkyl, halo-lower alkyl, or lower alkoxyalkylene.

9. A compound according to claim 1 wherein $R_1$, $R_2$, $R_3$, $R_4$ and $R_5$ are amido.

10. A compound according to claim 1 wherein $R_1$, $R_2$, $R_3$, $R_4$ and $R_5$ are lower alkoxy carbonyl.

11. A compound according to claim 1 having the structure

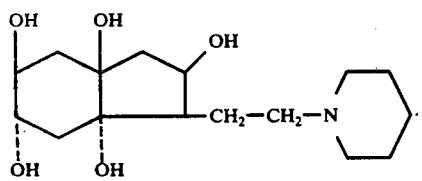

12. A compound according to claim 1 having the structure

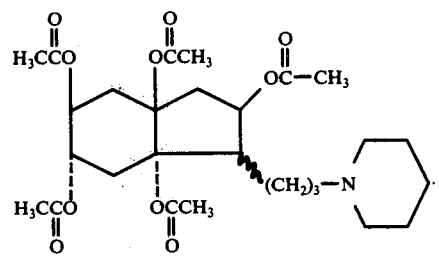

13. A compound according to claim 1 having the structure

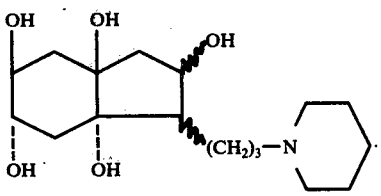

14. A compound according to claim 1 having the structure

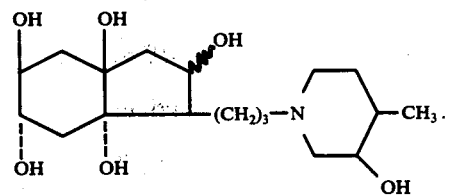

15. A compound according to claim 1 having the structure

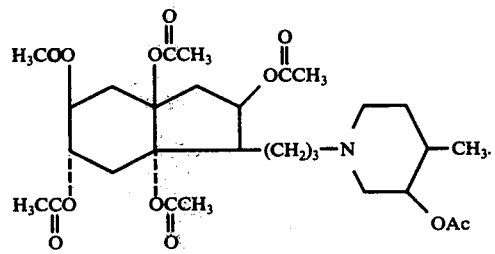

16. A compound according to claim 1 wherein $R_5$ is H and $R_1$, $R_2$, $R_3$ and $R_4$ are lower alkanoyl.

17. A hypertensive composition comprising an effective amount of compound as defined in claim 1 and a pharmaceutically acceptable carrier thereof.

18. A method of treating hypertension in mammalian species, which comprises administering to a mammalian host a therapeutic amount of the composition as defined in claim 17.

* * * * *

UNITED STATES PATENT OFFICE
CERTIFICATE OF CORRECTION

Patent No. 4,053,596     Dated October 11, 1977

Inventor(s) Frederic Peter Hauck et al.

It is certified that error appears in the above-identified patent and that said Letters Patent are hereby corrected as shown below:

On the Abstract page, under Inventors, delete the following:
  "Venkatachala L. Narayanan, Hightstown, Christopher M. Cimarusti, Hamilton; Rudiger D. Haugwitz, Titusville".
Column 1, line 58, after "monocyclic cycloalkyl-lower" insert --alkyl--.
Column 3, line 4, "from" should read --form--.
Column 4, line 57, "of" should read --or--.
Column 5, line 15, "in" should read --$\sim$--.
Column 5, line 16, "in" should read --$\sim$--.
Column 9, line 4, "aminioalkyl" should read --aminoalkyl--.
Column 14, line 68, "$\geq$" should read --$\leq$--.

Column 15, line 34, after "4a,8a" insert -- -trans-5-[3-(dimethylamino)propyl]decahydro-2,3,4a,6,8a --.
Column 15, line 48, "$\leq$" should read --$\leq$--.

Column 16, line 6, "50" should read --150--.
Column 16, line 8, "dih-" should read --dich- --.
Column 16, line 21, "ahydro2" should read --ahydro-2--.
Column 16, line 42, before the title insert --B.--.
Column 19, line 17, "4261" should read --4621--.
Column 21, line 41, "7M" should read --1M--.
Column 21, line 67, before "hydroxy" insert --(3- --.
Column 22, line 68, "II" should read --III--.
Column 24, Example 13, last column, the formula should read
  -- -NH$_2$ --.
Examples 27 to 33 should be inserted before the headings
  set out at the top of columns 25 and 26.

UNITED STATES PATENT OFFICE
CERTIFICATE OF CORRECTION

Patent No. 4,053,596         Dated October 11, 1977

Inventor(s) Frederic Peter Hauck et al.

It is certified that error appears in the above-identified patent and that said Letters Patent are hereby corrected as shown below:

Columns 31 and 32, Example 136, the formulae in columns entitled "X-Y" should read

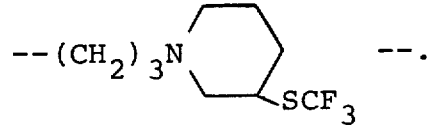

Column 33, in the structure at the top of Column 1, "$-R_6)_m$" should read -- $-(R_6)_m$ --.

Column 34, Example 144, under column entitled "$R_6$(position)", second occurrence, insert --$C_2H_5$(2)--.

Column 35, line 4, "7a" should read --8a--.

Column 38, line 54, after "of" insert --a--.

Signed and Sealed this

Seventh Day of March 1978

[SEAL]

Attest:

RUTH C. MASON
Attesting Officer

LUTRELLE F. PARKER
Acting Commissioner of Patents and Trademarks